United States Patent

Yeo et al.

Patent Number: 5,356,626
Date of Patent: Oct. 18, 1994

[54] SYNTHETIC FECAL FLUID COMPOUND

[75] Inventors: Richard S. Yeo, Dunwoody; Debra N. Welchel, Alpharetta, both of Ga.

[73] Assignee: Kimberly-Clark Corporation, Neenah, Wis.

[21] Appl. No.: 69,661

[22] Filed: Jun. 1, 1993

Related U.S. Application Data

[63] Continuation of Ser. No. 806,063, Dec. 11, 1991, abandoned.

[51] Int. Cl.⁵ .................. A61K 9/08; A61K 31/79; A61K 35/78
[52] U.S. Cl. .................. 424/195.1; 424/78.24
[58] Field of Search .......... 523/105; 524/15, 9; 424/195.1, 78.24, 78.01; 514/892

[56] References Cited

U.S. PATENT DOCUMENTS

| | | | |
|---|---|---|---|
| 4,104,214 | 8/1978 | Meierhoefer | 523/105 |
| 4,166,051 | 8/1979 | Cilento et al. | 260/17.4 |
| 4,272,514 | 6/1981 | Spence | 523/105 |
| 4,321,263 | 3/1982 | Powell et al. | 424/195.1 |
| 4,454,055 | 6/1984 | Richman et al. | 252/194 |
| 4,495,082 | 1/1985 | Mita et al. | 252/194 |
| 4,501,834 | 2/1985 | Su | 523/105 |
| 4,540,510 | 9/1985 | Karl | 252/315.3 |
| 4,551,331 | 11/1985 | Rudin | 424/195.1 |
| 4,584,188 | 4/1986 | Graham | 523/105 |
| 4,619,831 | 10/1986 | Sharma | 426/93 |
| 4,824,681 | 4/1989 | Schobel et al. | 426/5 |
| 4,839,215 | 6/1989 | Starling | 523/105 |
| 4,859,719 | 8/1989 | Ofstead | 523/105 |
| 4,978,529 | 12/1990 | Denick, Jr. | 424/195.1 |
| 4,999,200 | 3/1991 | Casillan | 424/195.1 |
| 5,078,994 | 1/1992 | Nair | 523/105 |
| 5,091,448 | 2/1992 | Hoslettler et al. | 523/130 |

FOREIGN PATENT DOCUMENTS

| | | | |
|---|---|---|---|
| 2951319 | 7/1981 | Fed. Rep. of Germany | 523/105 |
| 8001384 | 7/1980 | World Int. Prop. O. | 523/105 |

*Primary Examiner*—Thurman K. Page
*Assistant Examiner*—Raj Bawa
*Attorney, Agent, or Firm*—Patrick C. Wilson

[57] ABSTRACT

Disclosed herein is a synthetic fecal fluid composition which is useful with respect to the development of personal care devices such as diapers, training pants and incontinence garments which serve to collect and contain fecal matter. The synthetic fecal fluid composition of the present invention has a greater ability to retain liquid thereby improving its simulation of the actual material. As a result, this material is an improvement over prior materials which dewatered too quickly and therefore acted as poor supplements for use in the testing and development of personal care products. the composition contains a mixture of approximately 70 to 90% by weight of liquid such as water and approximately 10 to 30% by weight of solids including both water-soluble and water-insoluble components.

2 Claims, No Drawings

SYNTHETIC FECAL FLUID COMPOUND

This application is a continuation of application Ser. No. 07/806,063 entitled "SYNTHETIC FECAL FLUID COMPOUND" and filed in the U.S. Patent and Trademark Office on Dec. 11, 1991, now abandoned.

BACKGROUND OF THE INVENTION

The present invention relates to a synthetic fecal fluid compound. More particularly it is a synthetic fecal fluid compound that has an improved dewatering rate thereby making it more useful than existing materials for testing and other procedures where fecal matter is involved. One particular area of usefulness is with respect to the development of personal care devices such as diapers, training pants and incontinence garments which serve to collect and contain fecal matter.

Many companies, such as the assignee of record, expend large sums of money in the development of and improvement in personal care products including diapers, training pants and incontinence garments. One of the primary criterion in the development of such products is their ability to collect and contain body fluids including urine and fecal matter. While it is often the case that end-of-term development of a new or improved product involves actual experimental consumer testing, much of the initial testing is done on a bench scale in the laboratories. In such situations it is not practical to use actual body fluids. As a result, synthetic materials and substitutes are used. Strange as it may seem, materials used in the past have included mashed potatoes, brownie mix, peanut butter and pumpkin pie filling. In fact, the need for such material is great enough that a synthetic formulation has been commercially produced and sold. SiliClone Studio of Valley Forge, Pa. has marketed a synthetic fecal fluid sold under the trademark FECLONE ®.

One problem in the use of the previously mentioned materials is their inability to mimic the actual material. Babies, as an example, excrete fecal matter which varies over a wide range of viscosities despite the fact that the water content stays fairly constant. This variance in viscosity/consistency is often due to the babies' diets, health and stage of development. Typically the water content stays within the range of 70 to 90 percent by weight and most typically at approximately 80 percent. By way of the present invention it has been found that the viscosity of the material is more dependent upon the weight percent of soluble and insoluble components as well as the molecular weight of the soluble component used to make the synthetic counterparts.

As mentioned at the outset, one major problem with synthetic fecal compounds and their substitutes is the fact that they release their water content or dewater too rapidly. Despite the apparent simplicity of personal care products, their actual structures are very complex. Their ability to absorb and retain body fluids is critically dependent upon the interaction of the various components of the product and their interaction with test fluids and compounds. As a result, the more inaccurate the properties are of the test fluids and compounds, the more inexact will be the testing within the lab. This in turn results in the need for more experimental use testing, higher costs and longer time periods for development. It is therefore and object of the present invention to provide a synthetic fecal fluid compound. It is another object of the present invention to provide a synthetic fecal fluid compound with a greater ability to retain water and therefore have a slower dewatering rate. These and other objects of the present invention will become more apparent upon a further review of the following specification and claims.

SUMMARY OF THE INVENTION

The present invention relates to a synthetic fecal fluid compound which has an improved dewatering rate thereby making it more useful than existing materials for testing and other procedures where fecal matter is involved. The material of the present invention can be made as a dry premix, as a concentrate or as a regular formulation depending upon the amount of liquid/water added to the solids component. To more closely mimic natural feces and in particular, runny bowel movements, the material of the present invention contains between approximately 70 and 90 percent water and more preferably about 80 percent water with the remainder of the formulation being a combination of both water-soluble and water-insoluble solids. As a general formulation the solids can include approximately 16 percent by weight of a water-insoluble component based upon the total solids weight and approximately 84 percent by weight of a water-soluble component based upon the total solids weight. In a more specific formulation the water-soluble component has an average molecular weight of 10,000 or greater and in yet another formulation at least 50 percent by weight of the water-soluble component has an average molecular weight of approximately 160,000 or greater.

The viscosity of the synthetic fecal fluid compound can be adjusted between about 1,000 and about 40,000 centipoise at 50 revolutions per minute with a more specific range from the standpoint of mimicking runny bowel movements being between about 3500 and about 5500 centipoise at 50 revolutions per minute. The dewatering rate can range between about 50 and about 400 grams per square meter per minute. To further improve the characteristics of the formulation a saturated fat can be added to the compound in an amount less than or equal to 2 percent by weight based upon the total weight of the compound. It also is possible to add antimicrobial agents or other food preservatives to retard decomposition and molding of the compound.

Suitable water-soluble components include, but are not limited to, polyvinyl pyrrolidone, polyvinyl alcohol, starch, natural gum, synthetic starch, chemically-modified starch, gelatin, agar and polyethylene oxide. Suitable water-insoluble components include, but are not limited to, hydrocolloids, natural insoluble fiber and ion exchange resins.

A specific synthetic fecal fluid compound comprises a mixture of approximately 70 to 90 weight percent water and approximately 10 to 30 weight percent solids based upon the total weight of the compound. The solids include approximately 16 percent by weight, based upon the total solids weight, of a water-insoluble component and approximately 84 percent by weight, based upon the total solids weight, of a water-soluble component. At least 50 percent by weight of the water-soluble component, based upon the total water-soluble component weight, has an average molecular weight of approximately 160,000 or greater. This compound has a viscosity of between about 3500 and about 5500 centipoise at 50 revolutions per minute and a dewatering rate of between about 350 and about 400 grams per square meter per minute.

If desired, the synthetic fecal fluid compound can be made as a premix. One such formulation would include a mixture of approximately 19 percent by weight of a water-insoluble component and approximately 81 percent by weight of a water-soluble component based upon the total solids weight.

One of the primary advantages of the present invention is the ability to adjust both the viscosity and the dewatering rate of the compound to more closely mimic natural feces. Past materials, such as mashed potatoes, brownie mix, peanut butter, pumpkin pie filling and commercially available material have not sufficiently bound the water to themselves and as a result release the water too quickly as compared to the natural material. In contrast, the material of the present invention upon proper formulation, more tightly binds the water and therefore acts as a better analog to the natural material.

DETAILED DESCRIPTION OF THE INVENTION

The present invention is directed to an improved synthetic fecal fluid compound which more closely simulates the fluid dynamics of natural feces. The effectiveness of a laboratory evaluation in predicting the in vivo performance of a synthetic material is directly proportional to the similarity in the behavior of the test fluid with its natural counterpart. In the case of feces, a major attribute which impacts the efficacy of the synthetic material is the level to which the water is bound within the structure of the compound. Using high viscosity materials it is possible to produce synthetic compounds which bind water. However, it is much more difficult to produce materials which meet certain water binding specifications and yet have low viscosity ranges, particularly in the range of 3500 to 5500 centipoise (cps).

Natural feces/stools in infants range from very runny, low viscosity materials to very high viscosity, solid materials. When testing the fluid absorption and transport rates of personal care products such as infant diapers, it has often been difficult to evaluate the performance of the personal care product when used in conjunction with synthetic materials which attempt to mimic runny feces, that is, feces having a viscosity in the range of 3500 to 5500 centipoise (cps). Actual clinical data indicates that infant feces routinely has a dewatering rate which does not exceed 50 grams per square meter per minute ($g/m^2/min$) regardless of fluid viscosity. Commercial fecal formulations and food stuff models typically dewater at rates greater than 500 grams per square meter per minute. For example, a pumpkin pie filling has a viscosity of 4040 cps and dewaters at a rate of 912 $g/m^2/min$. The pumpkin pie filling is safe for use in product testing but it does not bind water strongly. Mashed potatoes can be mixed with water to generate materials having a solids content of about 11 percent, a viscosity of approximately 1100 cps and a dewatering rate of approximately 650 $g/m^2/min$. Peanut butter is another substitute food stuff model which when mixed with water is approximately 56 percent solids, has a viscosity of approximately 20,000 cps and a dewatering rate of approximately 180 $g/m^2/min$. Peanut butter offers the benefit of consistency but is often undesirable due to its high oil content. In addition to these food stuff materials, a synthetic fecal material is available which contains, on a weight percentage basis based upon the total weight of the material, 80% water and 20% solids. The solids component contains 65.1% of a powdered cellulose manufactured by the James River Corporation of Berlin, N.H., and sold as Solka-Floc BW-100; 11% wheat bran which had been sieved through a screen having approximately 1 mm size openings; 6.6% Fiberall ® psyllium hydrophilic mucilloid; 10.9% poly(oxyethylene) powdered material manufactured by Union Carbide Corporation, Specialty Chemicals Division, Danbury, Conn., and sold as Polyox Water-Soluble Resin WSR-N750, and 0.1% poly(oxyethylene) Polyox WSR-301, also from the same company; 0.7% potassium sorbate; 2.8% burnt sienna, which is a calcined natural earth dry pigment (reddish-brown iron oxide); 1.4% yellow ocher, which is a natural earthy dry pigment (yellowish hydrous iron oxide with alumina and silica); and 1.4% raw umber, which is a natural earth compound which consists chiefly of the hydrous silicates and oxides of iron and manganese. This material has a viscosity ranging from approximately 2276 to 4032 centipoise and a dewatering rate of 524 to 535 grams per square meter per minute. In contrast, the materials of the present invention when adjusted to a viscosity range of 3500 to 5500 centipoise have a dewatering rate ranging from between about 350 to about 400 grams per square meter per minute.

TEST PROCEDURES

The viscosity of each of the materials discussed herein was measured in centipoise at 50 revolutions per minute using a model RVT viscometer manufactured by Brookfield Engineering Laboratories, Inc., Stoughton, Mass. The dewatering rate was measured in grams per square meter per minute ($g/m^2/min$). Assessment of the dewatering rate of a compound was achieved by placing a 2 gm sample of the compound in contact with an absorbent material and measuring the amount of fluid which was released by the compound and absorbed by the absorbent material. The absorbent material used in the testing was a 2.65 ounce per square yard, 3 micron average denier fine fiber polypropylene meltblown nonwoven batt. The meltblown batt was treated with Aerosol OT-75 and Igepal R520 surfactants at a ratio of 9:1 and an add-on level of 0.5% by weight. Aerosol OT is manufactured by American Cyanamid Company of Wayne, N.J. while Igepal R250 is manufactured by GAF Chemicals Company of Spartanburg, S.C. Other materials required for the test included a plexiglass plate 6×5 inches with a thickness of ⅛ of an inch and having a 1 inch×1 inch square opening. A polyester net of 20 to 50 mesh was used to capture the sample compound solids for removal. In performing the test, the separation net, having a size of approximately 3×3 inches, was placed over the pre-weighed absorbent immediately beneath the opening in the plexiglass plate. The compound sample was then placed uniformly into this opening such that 2.05 cubic centimeters of the test fluid was applied. (A large amount of sample compound was used to overfill the opening and the excess sample was removed by drawing a putty knife over the open area in the plexiglass plate). The test compound was allowed to contact the absorbent for two minutes after which it was removed from the absorbent material along with the plexiglass plate and the separation net. The purpose of the separation net was to restrict, as much as possible, the actual transfer of any of the solids portion of the compound to the absorbent below. A weight by difference of the absorbent was then taken and the dewatering rate was calculated by dividing the increase in weight of the absorbent in grams by the open area of the plexiglass plate ($6.45 \times 10^{-4} m^2$) in square meters by the length of time in minutes (2 minutes). The result was the number of grams per square meter per minute of liquid which was removed from the test compound sample.

EXAMPLES

Table 1 contains data generated with various experimental compound formulations. A total of thirty-two examples are presented in Table 1. Examples 1 through 4 represent formulations made using the commercially available FECLONE® BFPS-4 powder from Sili-Clone Studio of Valley Forge, Pa. As can be seen with respect to all the examples, the weight percent liquid/water ranged from a low of 34 weight percent in Example 20 to a high of 99.8 weight percent in Example 18. In the majority of the examples, the liquid content was approximately 80 weight percent. In Examples 1 through 17 the predominant solids component was the FECLONE® BFPS-4 dry mix which is a combination of both water-soluble and water-insoluble components. More specifically, this dry mixture contains 65.1% of a powdered cellulose manufactured by the James River Corporation of Berlin, N.H. and sold as Solka-Floc BW-100; 11% wheat bran which had been sieved through a screen having approximately 1 mm size openings; 6.6% Fiberall® psyllium hydrophilic muccilloid; 10.9% poly(oxyethylene) powdered material manufactured by Union Carbide Corporation, Specialty Chemicals Division, Danbury, Conn., and sold as Polyox Water-Soluble Resin WSR-N-750, and 0.1% poly(oxyethylene) Polyox WSR-301, also from the same company; 0.7% potassium sorbate; 2.8% burnt sienna, which is a calcined natural earth dry pigment (reddish-brown iron oxide); 1.4% yellow ocher, which is a natural earthy dry pigment (yellowish hydrous iron oxide with alumina and silica); and 1.4% raw umber, which is a natural earth compound which consists chiefly of the hydrous silicates and oxides of iron and manganese. The standard FECLONE® material is shown in Examples 1 through 4 and has a viscosity in the range of 2276 to 4032 cps with a dewatering rate of approximately 524 to 535 grams per square meter per minute.

Formulation of the synthetic fecal compounds involved several slightly different methods. For Examples 1 through 4, the FECLONE® BFPS-4 dry mix was simply added to water, stirred and heated to a temperature below boiling (100° C.). For Examples 5 through 17, the FECLONE® BFPS-4 dry mix was added to approximately half of the overall water used. The remaining water was then mixed with the other components. Following this, the two separate mixtures were added together and stirred to make the final formulation. For those of the Examples using gelatine, agar, guar gum, Airvol 125 and Penford Gum 380, the mixture was heated while being stirred. No heating was needed for those formulations using the WATER-LOCK® J500. Examples 18 through 32 used none of the FECLONE® BFPS-4 dry mix. In these formulations, the indicated components were added to the water and stirred to create the various formulations. Note, however, that those formulations which used the Penford Gum 380 (Examples 22 through 27) and the high molecular weight polyvinyl pyrrolidone (Examples 28 through 32) also used the addition of heat to assist in the formulation of the sample materials. Generally speaking, where heat was necessary, the temperature of the solution was elevated to a temperature slightly below boiling (100° C.).

The gelatine, agar and guar gum were all obtained from the Aldrich Chemical Company of Milwaukee, Wis. The Airvol 125 hot water-soluble polyvinyl alcohol was obtained from Air Products and Chemicals of Allentown, Pa. The Penford Gum 380 hydroxyethyl ether derivative of cornstarch was obtained from Penick & Ford Ltd. of Cedar Rapids, Iowa. The WATERLOCK® J500, which is a poly(sodium acrylate) superabsorbent was obtained from the Grain Processing Corporation of Muscatine, Iowa. The Dowex® HCR-S and Dowex® HCR-S-H ion exchange resins were both obtained from the Dow Chemical Company of Midland, Mich. The Fiberall® psyllium hydrophilic muccilloid is a commercially available product which is distributed by Rydelle Laboratories, Inc. of Racine, Wis. Both the low molecular weight (10,000) and high molecular weight (160,000) polyvinyl pyrrolidone polymers were obtained from the Aldrich Chemical Company of Milwaukee, Wis.

As demonstrated by the data contained in Table 1, low dewatering rates at high (greater than 10,000 centipoise) viscosities was achieved in Examples 6, 7, 8, 9, 10, 13, 19, 20, 21, 22 and 23. The high dewatering rates in Examples 20 and 21 was presumably due to the fact that these ion exchange resins can absorb more than 4 times their own weight in water but the absorbed water is not strongly bound to the ionic groups.

From the data contained in Table 1 it was discovered that a proper mixture of both water-soluble and water-insoluble components was necessary to achieve low dewatering rates while keeping the weight percent water relatively constant between approximately 70 and 90 percent by weight and preferably at approximately 80 percent by weight. This could be achieved by making the water-insoluble component of the total solids content approximately 16 percent by weight, based upon the total solids weight, and the water-soluble component approximately 84 percent by weight, based upon the total weight of the solids. This in turn translated into a water-insoluble component weight percent of approximately 3 percent based upon the total weight of the compound (solids and liquids) and a weight percent of approximately 17 percent for the water-soluble component based upon the total weight of the compound (solids and liquids). In addition, it was found that the dewatering rate could be affected by the molecular weight of the water-soluble component used in the compound. Normally, water-soluble components which had an average molecular weight of 10,000 or greater appeared to work better. Results were improved even more when at least 50 percent of the water-soluble component based upon the total weight of the water-soluble component had an average molecular weight of approximately 160,000 or greater. See Examples 31 and 32.

Several water-soluble components which can be used with the present invention include, but are not limited to, polyvinyl pyrrolidone, polyvinyl alcohol, starch, natural gum, synthetic starch, chemically modified starch, gelatin, agar and polyethylene oxide. Suitable water-insoluble compounds include, but are not limited to, hydrocolloids, natural water-insoluble fiber, ion exchange resins and powdered cellulose.

As can be seen from Table 1, the present invention can be made to mimic fecal matter over a wide variety of viscosities from runny bowel movements to hard stools. Thus the present invention can be used to make synthetic fecal fluid compounds ranging in viscosities from about 1,000 to 40,000 centipoise. It also has been found that other additives can be incorporated into the compound to further modify its properties. For example, by adding a saturated fat to the solids portion of the compound in a weight percent of 2 percent or less, based upon the total weight of the compound, results in a reduction in both the surface tension and the dewatering rate of the compound. To extend the shelf life of the material, the formulator may want to consider adding an antimicrobial agent or other food preservative additives to retard decomposition and molding of the material prior to its use.

It should be noted that while the synthetic fecal fluid compound of the present invention is used when mixed with water, it is also possible to make a dry pre-mix devoid of water or a concentrate with very little liquid which can then be added to water to form the end product. A particularly preferred compound, using a weight percent based upon the total weight of the compound, includes approximately 80 percent water, approximately 15 percent polyvinyl pyrrolidone and approximately 5 percent psyllium hydrophilic muccilloid with at least 50 percent by weight of the polyvinyl pyrrolidone having an average molecular weight of approximately 160,000 or greater. Another preferred compound as shown in Examples 16 and 17 uses a precooked starch to replace a portion of the BFPS-4 commercial mixture solid while maintaining the total solids at the targeted 20% value. This compound demonstrated dewatering rates in the range of 330 to 350 grams per square meter per minute while having a viscosity ranging from about 4500 to 5520 centipoise.

To further demonstrate the improved properties of the present invention, another type of fluid transport test was performed. In this test, the object was to see how much of the synthetic fecal fluid compound or any of its components, such as water, would pass through an absorbent medium under pressure. With natural feces under pressure against an absorbent medium, the amount of feces which passes directly through the absorbent medium will depend upon both the basis weight of the medium and the water-retentive properties of the fecal matter. Natural feces, when placed under pressure against a meltblown nonwoven web having a basis weight of 2.5 ounces per square yard passes very little of its material through the absorbent medium. However, as the basis weight of the nonwoven medium is decreased, the ability of the natural feces to make its way through the medium increases. By way of comparison, however, the previously available formulation of synthetic fecal matter such as shown in Examples 1-4 passed on average approximately 25% of its weight through the same basis weight nonwoven medium under the same test. This transport of material was primarily the water which was released from the synthetic fecal compounds. In contrast, the material of the present invention, and in particular the compounds of Examples 16 and 17, allowed much less material pass through the meltblown medium under the same circumstances as compared with the FECLONE ® synthetic fecal matter of Examples 1-4. When using a 2.5 ounce per square yard meltblown as the absorbent medium, the material of Examples 1 through 4 when placed under pressure allowed at least 23% of its weight, primarily in the form of water, to be transported through the absorbent material. In contrast, using the same basis weight material, the material of Examples 16 and 17 only allowed 3.2% of its overall weight to be passed through the absorbent material. When decreasing the basis weight of the meltblown material to 1.7 ounces per square yard, the same material from Examples 1 through 4 again passed approximately 24% of itself through the absorbent material while, in contrast, the synthetic fecal matter in Examples 16 and 17 only allowed 6.5% of the compound to pass through the absorbent material. Finally, when the weight of the meltblown absorbent material was reduced to 0.9 ounces per square yard, the percentage of the material in Examples 1 through 4 which was transported through the absorbent material increased to almost 28%, while the material from Examples 16 and 17 only allowed approximately 11% of its weight to be passed through the absorbent material. As a result, this test showed that there is a higher correspondence between the material of the present invention to natural feces as compared to the predecessor material shown in Examples 1 through 4. These results are shown in Table 2.

From the foregoing it can be seen that the material of the present invention provides a synthetic fecal fluid compound which comes closer to mimicking the natural product than the preceding materials. The viscosity of the material can be varied over a wide range while still maintaining improved dewatering rates. In the range of 3500 to 5500 centipoise, the material of the present invention is more able to mimic the characteristics of runny feces while still exhibiting an improved dewatering rate which is most typically in the range of 300 to 400 grams per square meter per minute. It also should be noted that the material of the present invention can be made as a pre-mix which is then added to water or it can be directly formulated with water to yield the end product.

Having thus describing the invention in detail it should be apparent that various modifications and changes can be made in the present invention without departing from the spirit and scope of the following claims.

TABLE 1

| Example | Water | Feclone BFPS-4 Dry Mix | Gelatine | Agar | Guar Gum | Airvol 125 | Penford Gum 380 | Water-lock ® J500 | Ion Exchange Resins HCR-S | HCR-S-H |
| --- | --- | --- | --- | --- | --- | --- | --- | --- | --- | --- |
| 1 | 80 | 20 | | | | | | | | |
| 2 | 80 | 20 | | | | | | | | |
| 3 | 80 | 20 | | | | | | | | |
| 4 | 80 | 20 | | | | | | | | |
| 5 | 80 | 19 | 1 | | | | | | | |
| 6 | 80 | 15 | 5 | | | | | | | |
| 7 | 80 | 19 | | 1 | | | | | | |
| 8 | 80 | 15 | | 5 | | | | | | |
| 9 | 80 | 18 | | | | | | | | |
| 10 | 80 | 18 | | | 2 | | | | | |

TABLE 1-continued

| | | | | | | | |
|---|---|---|---|---|---|---|---|
| 11 | 80 | 18 | | 2 | | | |
| 12 | 86 | 9 | | 5 | | | |
| 13 | 77 | 18 | | 5 | | | |
| 14 | 82 | 11 | | 7 | | | |
| 15 | 76 | 20 | | | 4 | | |
| 16 | 80 | 15 | | | 5 | | |
| 17 | 80 | 15 | | | 5 | | |
| 18 | 99.8 | | | | | 0.2 | |
| 19 | 98 | | | | | 2 | |
| 20 | 34 | | | | | | 66 |
| 21 | 45 | | | | | | | 55 |
| 22 | 79 | | | | 20 | 1 | |
| 23 | 79.6 | | | | 19.9 | 0.5 | |
| 24 | 79.9 | | | | 20.0 | 0.1 | |
| 25 | 79.9 | | | | 19.9 | 0.2 | |
| 26 | 78 | | | | 19 | | |
| 27 | 80 | | | | 15 | | |
| 28 | 80 | | | | | | |
| 29 | 80 | | | | | | |
| 30 | 80 | | | | | | |
| 31 | 80 | | | | | | |
| 32 | 80 | | | | | | |

| Example | Psyllium Hydrophillic Muccilloid | Polyvinyl Pyrrolidone lmw | Polyvinyl Pyrrolidone hmw | Solution Viscosity (cps) | Dewatering Rate (G/M2/Min) |
|---|---|---|---|---|---|
| 1 | | | | 2276 | 535 |
| 2 | | | | 3536 | 524 |
| 3 | | | | 4032 | 534 |
| 4 | | | | 3128 | 531 |
| 5 | | | | 4184 | 357 |
| 6 | | | | 35120 | 128 |
| 7 | | | | 11360 | 295 |
| 8 | | | | Solid | 27 |
| 9 | | | | 10100 | 364 |
| 10 | | | | 40000 | 74 |
| 11 | | | | 9440 | 283 |
| 12 | | | | 1968 | 752 |
| 13 | | | | 23760 | 310 |
| 14 | | | | 5608 | 547 |
| 15 | | | | 7344 | 280 |
| 16 | | | | 4920 | 338 |
| 17 | | | | 5520 | 307 |
| 18 | | | | 2592 | 578 |
| 19 | | | | Solid | 3 |
| 20 | | | | Solid | 640 |
| 21 | | | | Solid | 1052 |
| 22 | | | | Solid | 31 |
| 23 | | | | 14760 | 233 |
| 24 | | | | 1184 | 739 |
| 25 | | | | 1804 | 605 |
| 26 | 3 | | | 3264 | No Data |
| 27 | 5 | | | 4872 | 307 |
| 28 | 2 | 9 | 9 | 1360 | 819 |
| 29 | 3 | 8.5 | 8.5 | 1376 | 721 |
| 30 | 4 | 8 | 8 | 3152 | 475 |
| 31 | 5 | 7.5 | 7.5 | 3480 | 382 |
| 32 | 6 | 7 | 7 | 5200 | 374 |

*Amount of each component is on a weight percent basis.

TABLE 2

| Meltblown Basis Weight Ounces per Square Yard | Weight Percent Feclone Transport | Weight Percent Modified Fluid Transport |
|---|---|---|
| 2.5 | 23.4 | 3.2 |
| 1.7 | 24.5 | 6.5 |
| 0.9 | 27.8 | 10.9 |

We claim:

1. A synthetic fecal fluid composition consisting of: approximately 80 percent by total weight water, approximately 15 percent by total weight polyvinylpyrrolidone and approximately 5 percent by total weight psyllium hydrophilic mucilloid.

2. The composition of claim 1 wherein at least 50% by weight of said polyvinylpyrrolidone has an average molecular weight of approximately 160,000 or greater.

* * * * *

UNITED STATES PATENT AND TRADEMARK OFFICE
CERTIFICATE OF CORRECTION

PATENT NO. : 5,356,626
DATED : October 18, 1994
INVENTOR(S) : Richard S. Yeo et al It is certified that error appears in the above-indentified patent and that said Letters Patent is hereby corrected as shown below:

Abstract, line 11, ". the" should read —. The—.

Signed and Sealed this

Seventeenth Day of October, 1995

Attest:

BRUCE LEHMAN

Attesting Officer

Commissioner of Patents and Trademarks